(12) United States Patent
Cetingul et al.

(10) Patent No.: US 10,088,544 B2
(45) Date of Patent: Oct. 2, 2018

(54) TRACTOGRAPHY FRAMEWORK WITH MAGNETIC RESONANCE IMAGING FOR BRAIN CONNECTIVITY ANALYSIS

(71) Applicant: Siemens Healthcare GmbH, Erlangen (DE)

(72) Inventors: Hasan Ertan Cetingul, Fulton, MD (US); Benjamin L. Odry, West New York, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 214 days.

(21) Appl. No.: 15/221,989

(22) Filed: Jul. 28, 2016

(65) Prior Publication Data

US 2017/0052241 A1    Feb. 23, 2017

Related U.S. Application Data

(60) Provisional application No. 62/205,905, filed on Aug. 17, 2015.

(51) Int. Cl.
| | |
|---|---|
| *G01R 33/563* | (2006.01) |
| *A61B 5/055* | (2006.01) |
| *A61B 5/00* | (2006.01) |
| *G06T 5/00* | (2006.01) |
| *G06T 7/30* | (2017.01) |
| *G06T 7/11* | (2017.01) |
| *G01R 33/56* | (2006.01) |

(52) U.S. Cl.
CPC ...... *G01R 33/56341* (2013.01); *A61B 5/0013* (2013.01); *A61B 5/0042* (2013.01); *A61B 5/055* (2013.01); *A61B 5/7271* (2013.01); *A61B 5/742* (2013.01); *G06T 5/002* (2013.01); *G06T 7/11* (2017.01); *G06T 7/30* (2017.01); *A61B 2576/026* (2013.01); *G01R 33/5608* (2013.01); *G06T 2207/10092* (2013.01); *G06T 2207/20128* (2013.01); *G06T 2207/30016* (2013.01)

(58) Field of Classification Search
CPC ...... G06T 7/30; A61B 5/0013; G01R 33/5608
See application file for complete search history.

(56) References Cited

U.S. PATENT DOCUMENTS

| | | | | |
|---|---|---|---|---|
| 2011/0199084 A1* | 8/2011 | Hasan | ...... | A61B 5/055 324/309 |
| 2012/0280686 A1* | 11/2012 | White | ...... | G01R 33/56341 324/309 |
| 2013/0113481 A1* | 5/2013 | Kim | ...... | G01R 33/56518 324/309 |

OTHER PUBLICATIONS

Bhushan, Chitresh, et al. "Co-registration and distortion correction of diffusion and anatomical images based on inverse contrast normalization." Neuroimage 115 (2015): 269-280.

(Continued)

*Primary Examiner* — Jermele M Hollington
*Assistant Examiner* — Alvaro Fortich (57) ABSTRACT

In white matter tractography from magnetic resonance imaging, a mathematical representation of diffusion (e.g., fiber orientation distributions) is first estimated from the diffusion MR data. Fiber tracing is performed via deterministic or probabilistic tractography where the tract maps and brain regions from multiple atlases and/or templates can be used for seeding and/or as spatial constraints. Field map correction and/or denoising may improve the diffusion weighted imaging data used in tractography.

13 Claims, 2 Drawing Sheets

(56) References Cited

OTHER PUBLICATIONS

Cui, Zaixu, et al. "PANDA: a pipeline toolbox for analyzing brain diffusion images." (2013).

Côté, Marc-Alexandre, et al. "Tractometer: towards validation of tractography pipelines." Medical image analysis 17.7 (2013): 844-857.

Glasser, Matthew F., et al. "The minimal preprocessing pipelines for the Human Connectome Project" Neuroimage 80 (2013): 105-124.

Grabner, Günther, et al. "Symmetric atlasing and model based segmentation: an application to the hippocampus in older adults." International Conference on Medical Image Computing and Computer-Assisted Intervention. Springer Berlin Heidelberg, 2006.

Greve, Doug. "FreeSurfer." Wiki. N.p., n.d. Retrieved Jul. 26, 2016, from http://surfer.nmr.mgh.harvard.edu/fswiki.

Jenkinson, M., Beckmann, C. F., Behrens, T. E., Woolrich, M. W., & Smith, S. M. (2012). Fsl. Neuroimage, 62 (2), 782-790.

Manjón, JoséV., et al. "Diffusion weighted image denoising using overcomplete local PCA." PloS one 8.9 (2013): e73021.

The Human Connectome Project. (n.d.). Retrieved Jul. 26, 2016, from http://www.humanconnectome.org/.

Tournier, J-Donald, et al."Resolving crossing fibres using constrained spherical deconvolution: validation using diffusion-weighted imaging phantom data." Neuroimage 42.2 (2008): 617-625.

Tournier, J., Fernando Calamante, and Alan Connelly. "MRtrix: diffusion tractography in crossing fiber regions." International Journal of Imaging Systems and Technology 22.1 (2012): 53-66.

Tzourio-Mazoyer, Nathalie, et al. "Automated anatomical labeling of activations in SPM using a macroscopic anatomical parcellation of the MNI MRI single-subject brain." Neuroimage 15.1 (2002): 273-289.

Zhang, Yajing, et al. "Atlas-guided tract reconstruction for automated and comprehensive examination of the white matter anatomy" Neuroimage 52.4 (2010): 1289-1301.

* cited by examiner

TRACTOGRAPHY FRAMEWORK WITH MAGNETIC RESONANCE IMAGING FOR BRAIN CONNECTIVITY ANALYSIS

RELATED APPLICATIONS

The present patent document claims the benefit of the filing date under 35 U.S.C. § 119(e) of Provisional U.S. Patent Application Ser. No. 62/205,905, filed Aug. 17, 2015, which is hereby incorporated by reference.

BACKGROUND

The present embodiments relate to magnetic resonance imaging (MRI). In particular, white matter tractography for brain connectivity analysis with magnetic resonance imaging is provided.

Diffusion tractography is a 3D modeling technique to visually represent neural tracts from diffusion magnetic resonance imaging (MRI) data. Tractography has gained importance in the medical imaging community for the last decade, especially with the initiation of the NIH Blueprint: Human Connectome Project. However, tractography is often used by the neuroscience community while ignoring error, lack of validation or other limitations. While various problems indirectly or directly related to tractography have been addressed (e.g., super-resolved diffusion MR images, better diffusion MRI preprocessing tools, representations that can reduce the errors due to the de facto tensor modeling in crossings and high curvature areas, and fast computation of full brain tractograms), other problems continue to be ignored.

Glasser, et al., in "The Minimal Preprocessing Pipelines for the Human Connectome Project Neuroimage," provides a benchmark in the research community for processing pipelines for brain connectivity analysis. These pipelines, not only for diffusion MR but also for functional MR datasets, constitute a sequential execution of several methods most of which are publicly available in third party tools. These methods for diffusion tractography may still be considered limited, such as due to processing efficiency. Another approach preprocesses the input diffusion data and finishes execution by aligning diffusion data with available structural MRI data, but does not provide a tractography pipeline. In yet another approach, a MATLAB® toolbox dedicated to diffusion MRI data performs preprocessing, tractography, extraction of diffusion metrics, and construction of brain networks. However, the only diffusion model in this approach is the diffusion tensor. The diffusion tensor may not be accurate in the case of partial volume effects and might jeopardize the reliability of the resulting brain networks.

BRIEF SUMMARY

By way of introduction, the preferred embodiments described below include methods, systems, instructions, and computer readable media for magnetic resonance imaging. By using tracts and brain region information from multiple atlases and/or templates, diffusion may be modeled with fiber orientation distributions from the diffusion MRI data. The resulting representations are utilized in deterministic or probabilistic tractography with the tracts and brain regions being used for seeding and/or as spatial constraints. Field map correction and/or denoising may improve the diffusion weighted imaging data used in the tractography.

In a first aspect, a method is provided for tractography with magnetic resonance imaging. A magnetic resonance imaging system scans a patient for diffusion weighted data. The scanning provides data without diffusion sensitization and in phase-encoded and reverse phase encoded directions. The diffusion weighted data is in a subject space. The magnetic resonance imaging system acquires structural magnetic resonance data. The diffusion weighted data is corrected with field maps estimated from the data acquired in the phase-encoded and reverse phase encoded directions. The corrected diffusion weighted data is denoised. A first atlas of tract maps is registered to the subject space. Regions of interest through which tracts of the tract maps pass are identified from a second atlas. A tractogram for the patient is generated from the denoised, corrected diffusion weighted data, the tract maps, and the regions of interest. An image of the tractogram is transmitted.

In a second aspect, a non-transitory computer readable storage medium has stored therein data representing instructions executable by a programmed processor for tractography with magnetic resonance imaging. The storage medium includes instructions for identifying brain regions of interest, tracts, and tract path spatial restrictions from atlases registered to a patient, determining a white matter mask for the patient, inputting diffusion weighted imaging data from a magnetic resonance imager, solving for fiber orientation distributions from the diffusion weighted imaging data, the brain regions of interest, the tracts, and the tract path spatial restrictions, and outputting a tractogram that is a function of the fiber orientation distributions.

In a third aspect, a magnetic resonance system includes a plurality of coils. A reconstruction processor is configured to reconstruct, from measures of the coils, a set of diffusion weighted volumes, including both phase-encoded and reverse phase-encoded, for a patient and a structural volume for the patient. A tractography processor is configured to generate a tractogram from the diffusion weighted volumes, the structural volume, an atlas of probabilistic tract paths, and an atlas of brain regions.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A tractography processing pipeline is provided for brain connectivity analysis. A tractography processing pipeline enables a more streamlined analysis of brain connectivity. The pipeline may be performed by the MRI scanner, providing deliverable in the form of a brain network to radiologists and neuroscientists. This pipeline includes the state-of-the-art preprocessing and registration tools, the use of a priori anatomical (a.k.a. atlas) information, and advanced diffusion MRI modeling and tractography methods for accurate, reliable, and reproducible analysis of brain connectivity. In addition, the pipeline may assist the users toward a fair validation of tractography.

The tractography processing pipeline accepts diffusion MRI and accompanying structural MRI data of a subject, carries out the state-of-the-art preprocessing steps on the data, uses a priori anatomical information from well-established or other brain atlases, and performs diffusion estimation and tractography to the input data given a set of parameters and spatial constraints. The output of the pipeline is a tractogram, such as a representation of a set of patient-specific fiber pathways in three dimensions. As the state-of-the-art changes, new components may be added into the existing modules for improved processing. Alternatively or additionally, new modules that are responsible for fiber clustering, biomarker/map generation, network construction, or other operations are added.

Figure 1:
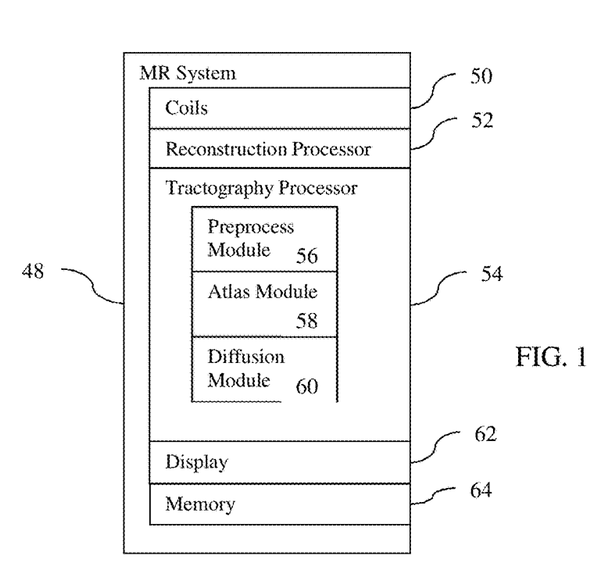
FIG. 1 is one embodiment of a magnetic resonance system for tractography.

FIG. 1 shows a magnetic resonance (MR) system 48. The system 48 includes coils 50, a reconstruction processor 52, a tractography processor 54, a display 62, and a memory 64. Additional, different, or fewer components may be provided. For example, a network or network connection is provided, such as for networking with a medical imaging network or data archival system. In another example, a user interface is provided. In yet another example, the reconstruction processor 52 and tractography processor 54 are implemented as one processor, such as a control processor, graphics processing unit, computer, or other component of the magnetic resonance imaging system 48.

The reconstruction and tractography processors 52, 54, memory 64, and display 62 are part of the medical imaging system 48. Alternatively, the reconstruction and tractography processors 52, 54, memory 64, and/or display 62 are part of an archival and/or image processing system, such as associated with a medical records database workstation or server. In other embodiments, the reconstruction and tractography processors 52, 54, memory 64, and/or display 62 are a personal computer, such as desktop or laptop, a workstation, a server, a network, or combinations thereof. The reconstruction and tractography processors 52, 54, memory 64, and/or display 62 may be provided without other components for tractography, such without the coils 50.

The MR system 48 includes a main field magnet, such as a cryomagnet, and gradient coils. Other processing components may be provided, such as for planning and generating transmit pulses for the coils 50 based on the sequence and for receiving and processing the received k-space data. In one embodiment, the MR system 48 is a 1.5-7 T clinical MR scanner, such as a MAGNETOM Aera, from Siemens AG, Erlangen, Germany. MR scanners from other manufactures and/or with other main field strengths may be used.

One or more coils 50 are provided and/or used. The coils 50 are a whole body coil, gradient coils, and/or one or more local coils.

The reconstruction and/or tractography processors 52, 54 are each a general processor, central processing unit, control processor, graphics processor, digital signal processor, three-dimensional rendering processor, image processor, application specific integrated circuit, field programmable gate array, digital circuit, analog circuit, combinations thereof, or other now known or later developed devices for MR reconstruction and tractography. The reconstruction and/or tractography processors 52, 54 are each a single device or multiple devices operating in serial, parallel, or separately. The reconstruction and/or tractography processors 52, 54 may be a main processor of a computer, such as a laptop or desktop computer, or may be a processor for handling some tasks in a larger system, such as in an imaging system. The reconstruction and tractography processors 52, 54 are each configured by instructions, design, hardware, and/or software to be able to perform the acts discussed herein, such as reconstruct MR volumes representing a patient and generate tractograms generated from the reconstructed volumes, respectively.

The reconstruction processor 52 is configured to reconstruct volumes from measurements from the coils 50. The coils 50 provide measurements in k-space. By controlling the MR system 48 or by acquisition of data by transfer or loading, the reconstruction processor 52 receives k-space data. By applying Fourier processing to the k-space data, the spatial distribution of response from the patient is reconstructed. The reconstructed data represent the patient volume or voxel regions distributed in three-dimensions within the patient.

Any reconstruction approach may be used. In one embodiment, diffusion weighted volumes are reconstructed, where sets are reconstructed without diffusion sensitization in phase-encoding (PE) and reverse PE directions. For example, b0 and b0r volumes are reconstructed. Any number of diffusion directions and corresponding frames of data (volumes) may be reconstructed, such as hundreds or thousands of frames of data. Structural data may be reconstructed, such as reconstructing with T1 weighting.

By scanning the patient with sequences specific to the type of reconstruction, the reconstruction processor 52 is configured to reconstruct volumes as sets of data representing different aspects (e.g., structural, diffusion, and/or functional) of the patient. The reconstruction processor 52 provides the scan data specific to a given patient. This scan data is to be used to determine a tractogram for the patient.

The tractography processor 54 is configured to generate a tractogram from the diffusion weighted frames, the structural frame, an atlas of probabilistic tract paths, and an atlas of brain regions. The reconstructed volumes as well as knowledge represented in the atlases are used for tractography. The knowledge represented in the atlases is represented as a collection or average and/or is represented as one or more templates.

Any of various tractography approaches may be used. Diffusion tensors may be estimated. In one embodiment, the tractogram is generated with constrained spherical deconvolution-based diffusion estimation of fiber orientation distribution. A region-of-interest guided deterministic or probabilistic tractography is performed by tracing or stepping along diffusion paths for each of a plurality of tracts. A white matter mask may limit the tractography. The fiber orientation distribution is estimated for each step or voxel along each of the tracts.

In one embodiment represented in FIG. 1, the tractography processor 54 implements a plurality of modules: preprocess module 56, atlas module 58, and diffusion module 60. Additional, different, or fewer modules may be provided. For example, modules are combined or further separated. As another example, additional modules for use of the tractogram (e.g., fiber clustering, network analysis, and/or biomarker modules) are added. A component of a module may be performed in a different module (e.g., denoising may be applied to the fiber orientation distributions in the diffusion module 60 rather than to the diffusion weighted data in the preprocessing module 56). The modules may contain additional components. For instance, the preprocessing module 56 may include components such as eddy current correction and motion correction, and the diffusion module 60 may include interpolation and peak detection or other diffusion metric.

The preprocessing module 56 carries out the preprocessing on diffusion MRI, as well as on the accompanying structural MRI data. Any preprocessing may be performed for the diffusion MRI, such as inhomogeneity (b0 and/or b0$r$ field map) correction and denoising. Any preprocessing may be performed for the structural MRI data, such as brain extraction, skull stripping, brain tissue segmentation (e.g., gray matter, white matter, and/or cortical spinal fluid (CSF) segmentation), and denoising.

The atlas module 58 integrates atlas knowledge or templates in the tractography. A priori anatomical knowledge in the form of an atlas annotation or template subject is integrated into tractography. By normalizing and spatially aligning the anatomical knowledge, the knowledge is incorporated into the tractography for the specific patient. In one example, an atlas (e.g., JHU-DTI-Prob) or a subject selected as template is registered with the structural data, and the resulting deformation provides an inversion of the knowledge into a subject space of the patient. The subject-warped atlas or atlases (i.e., knowledge warped into the subject space) is used for brain parcellation, such as identifying regions of interest (e.g., from AAL). Binary images (e.g., ROIs, average tract maps, or other information) are generated from the knowledge as spatial constraints for the patient to guide tractography.

The diffusion module 60 is a diffusion tractography module. Diffusion is estimated in tractography given a set of tractography tuning parameters and spatial constraints. In one example, the diffusion model (e.g., tensors or fiber orientation distribution) is reconstructed at each white matter voxel of the diffusion weighted imaging frames. The reconstruction uses deterministic or probabilistic tractography given a set of tuning parameters (e.g., step size, maximum local curvature, minimum fractional anisotropy, or other limitations in the tract tracing) and spatial constraints (e.g., seed image and/or regions to be included and excluded for a particular white matter tract and the tract).

The memory 64 is a graphics processing memory, a video random access memory, a random access memory, system memory, random access memory, cache memory, hard drive, optical media, magnetic media, flash drive, buffer, database, combinations thereof, or other now known or later developed memory device for storing data or image information. The memory 64 is part of the MR system 48, part of a computer associated with the one or both of the reconstruction and tractography processors 52, 54, part of a database, part of another system, a picture archival memory, or a standalone device.

The memory 64 stores data representing the brain of the patient. The stored data represents a three-dimensional region of the patient. The data is MR data, such as k-space or object space data. The data is diffusion data, such as b0, b0$r$, and diffusion weighted volumes, and/or the data is structural data, such as T1 or b0 and b0$r$ data. The data is from scanning the patient by the MR system 48. The memory 64 may alternatively or additionally store data during processing, such as storing masks, regions of interest, atlas information, tracts, tractography tuning parameters, field maps, corrected data, denoised data, tensors, fiber orientation distributions, nonlinear spatial transforms, segmentations, tractogram, and/or an output image.

The memory 64 or other memory is alternatively or additionally a computer readable storage medium storing data representing instructions executable by the programmed processor 50 for tractography with magnetic resonance imaging. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 54 is a monitor, LCD, projector, plasma display, CRT, printer, or other now known or later developed devise for outputting visual information. The display 54 receives images, graphics, or other information from the reconstruction processor 52, the tractography processor 54, memory 64, or MR system 48. One or more MR images are displayed, such as displaying a tractogram, fiber cluster representation, constructed network, or biomarker map.

Figure 2:
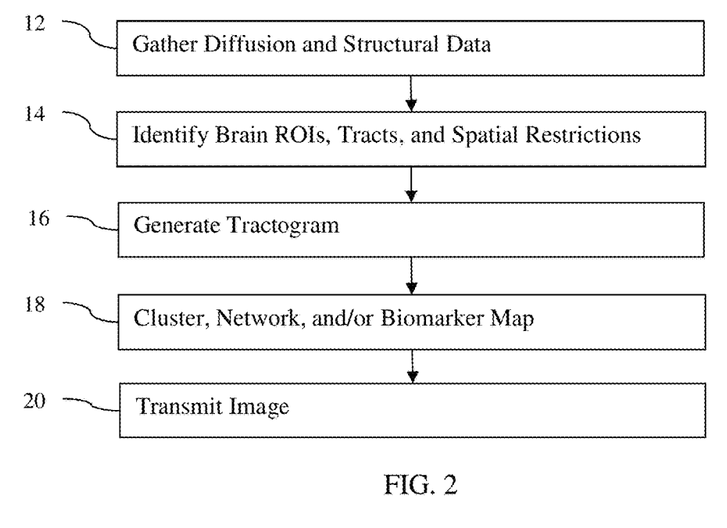
FIG. 2 is a flow chart diagram of one embodiment of a method for tractography with magnetic resonance imaging.

FIG. 2 shows a flow chart of a method for tractography with magnetic resonance imaging. Tractography uses diffusion weighted information with additional knowledge about tracts, brain regions of interest, and/or other spatial restrictions or probabilities to generate the tractogram. The tractogram is generated using fiber orientation distributions or other function representing diffusion across many frames or sets of data of diffusion at different directions. Denoising or other preprocessing may be performed on the gathered diffusion weighted imaging data in order to improve the tractogram.

Figure 3:
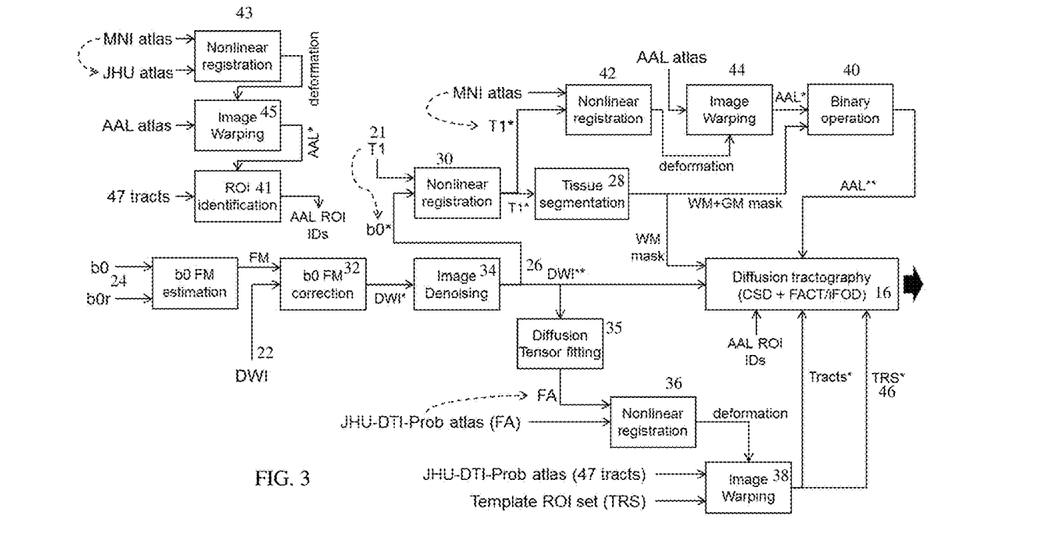
FIG. 3 is a flow chart diagram of another embodiment of the method for tractography with magnetic resonance imaging.

FIG. 3 is a flow chart of one embodiment of the method of FIG. 2. FIG. 3 illustrates an example tractography processing pipeline. Each block represents either a module (e.g., diffusion tractography) or a component (e.g., tissue segmentation). The dashed lines show the "direction" of registration (from "subject" to "template" where the arrow direction indicates the reference). FIGS. 2 and 3 are discussed below as one example. Other embodiments of the method of FIG. 2 may be provided.

The methods are implemented by the system of FIG. 1 or another system. For example, the methods are implemented on a computer or processor associated with a MRI system or PACS. The magnetic resonance system, using coils connected with transmitters and receivers, gathers the diffusion and structural data by scanning a patient and reconstructing. A memory provides the template or other knowledge of any number of atlases. A processor preprocesses the reconstructed data, identifies knowledge for the specific patient, generates the tractogram, and performs any further operations (e.g., see act 18). The processor and/or an interface (e.g., display plane for a display, memory interface, or network interface card) transmits any image. Other distributions of functions among components may be used.

The acts are performed in the order shown or other orders. For example, acts 12-20 are performed in numerical sequence. In the example of FIG. 3, acts 21, 30, 28, 42, 44, and 40 are performed after act 34 but may be performed prior to, after, or in parallel with acts 35, 36, 38, and 46. Similarly, act 28 may be performed prior to, after, or in parallel with acts 42, 44, and 40. Acts 24 and 22 are performed in any order. Acts 43, 45, and 41 are performed any time prior to act 16.

The acts are performed with the patient in the MRI system, such as laying in a generally uniform main magnetic field. Alternatively, the acts directly relying on scanning the patient (e.g., acts 21, 22 and 24) are performed with the patient in the MRI system, but other acts are performed with the patient out of the MRI system.

Additional, different, or fewer acts may be provided. For example, the transmission of an image in act 20 is not provided, but instead the tractogram or other information are provided without imaging. As another example, other acts for reconstruction, configuration, use of results, or other operation of the pipeline are provided. In yet another example, other preprocessing is provided.

In act 12, data representing a specific patient is gathered. One or more scans are performed by the magnetic resonance system. In response to application of magnetic fields and one or more pulses, data representing an interior region of a patient is acquired. By transmitting from and/or receiving signals at any of the MRI coils, k-space data is acquired. For example, the k-space data is acquired using a time-interleaved, multi-coil dynamic imaging sequence of pulses. As another example, the k-space data is acquired as frames or shot divisions of k-space data. Any now known or later developed MR scan sequence may be used.

A volume, frame, set of data, or image of the patient is reconstructed from the k-space data. Any reconstruction is performed. The data is directly estimated from the k-space data. The reconstruction provides data representing a three-dimensional or volume region of the patient. Values for voxels representing the volume at a given time or for a given scan form a frame of data or the volume data.

For tractography, the reconstructed data includes diffusion data (diffusion weighted images (DWI) and images without diffusion sensitization (b0, b0r)) and structural data (e.g., T1). The MR system or imager inputs diffusion weighted imaging data and structural data to the tractography pipeline. Any now known or later developed diffusion weighted scan sequence and reconstruction may be used. Any now known or later developed structural data scan sequence and reconstruction may be used. The diffusion and structural data may be reconstructed from the same or overlapping k-space data, or separate scans are used for separate types of data.

The gathering of the data for the patient may include preprocessing of the data to improve tractography. In one embodiment, field maps are estimated from data acquired along phase-encoded and reverse phase-encoded directions in order to correct the diffusion data with the field maps. The diffusion data is denoised after the field map correcting, and then the diffusion data as field map corrected and denoised is input to tractography. Additional, different, or fewer preprocessing operations may be performed.

FIG. 3 shows one example gathering of the diffusion and structural data. In act 21, the patient is scanned to acquire structural data. In the example of FIG. 3, the MRI system acquires the structural data as T1 data, but other structural data may be used.

In act 22, the patient is scanned to acquire diffusion weighted data. The MRI system performs diffusion magnetic resonance imaging to scan and reconstruct tens, or hundreds of volumes or sets of data representing diffusion in different directions within the patient.

Since the patient is scanned, the acquired data is in the subject or patient space. The coordinate system of the MRI imager provides a subject space. The templates or atlas information are in a generic world space, not the subject space. The data acquired by scanning the patient, at least at one time, is in the subject space. Motion correction may be applied to the data from different scans to normalize to one subject space.

In act 24, the MRI system acquires diffusion magnetic resonance data without diffusion sensitization and in phase-encoded (PE) and reverse phase encoded directions. For example, two frames of data are acquired. Each reconstructed volume includes data without diffusion sensitization. The data represents information acquired in phase-encoding and reverse PE directions. For example, b0 and b0r volumes are acquired. The data is acquired to estimate field maps (FMs) in rad/s. In other embodiments, only b0 in the PE direction is acquired rather than both b0 and b0r. Other types of volumes for estimating one or more field maps may be acquired.

Other structural data representing the patient may also or alternatively be acquired. For example, T1 weighted scanning and resulting T1 frame of data representing the patient is acquired. This structural data may be used to register with information not in the subject space. In the embodiment of FIG. 3, the b0 frame is treated as the reference subject space. As a result, act 30 registers the T1 frame with the b0 frame. Other frames may be treated as the reference subject space.

In act 32, the diffusion weighted data is corrected. Field map correction is applied. The diffusion weighted data in the PE and reverse PE directions is corrected. The field maps estimated from the b0 and b0r data are used to correct the diffusion weighted data.

In act 34, the field map corrected diffusion weighted data is denoised. Any denoising may be used. For example, a local principle component analysis-based method is applied to remove or reduce noise in the diffusion weighted data.

In act 26, skull and other non-brain regions are masked from the pre-processed diffusion data. Using one or more of the frames of the image data, locations in the volume or patient's head corresponding to the skull are identified. For example, a brain mask is obtained from field map-corrected, denoised b0 image. Thresholding or other skull stripping methods are used to identify the locations of the skull for masking. Once the mask is created, data in the diffusion weighted images corresponding to non-brain locations is removed or labeled as non-brain.

In act 28, further segmentation is performed for guiding the tractography. The tracts are specific to white matter, so the locations of other tissue and/or the location of white matter are determined. For example, a white matter mask is created by segmenting out or identifying white matter locations. The white matter mask is provided as an input to spatially constrain tractography.

A white matter-gray matter mask is also created by segmenting out or identifying both white and gray matter. The white matter-gray matter mask may be used to identify regions of interest in the brain in act 40. For example, a logical operation "AND" is applied between each of the labeled regions in the AAL atlas and the WM-GM mask of the subject in act 40 to further adjust or tune each AAL region to the subject.

A white matter-gray matter interface may be identified by segmentation or comparison of the white matter mask with the white matter-gray matter mask. The white matter-gray matter interface may be used as a spatial constraint or boundary for tractography.

Other segmentation may be provided. Any type of segmentation may be used, such as thresholding, pattern matching, machine-learnt classification, or random walker processing. The segmentation may or may not be seeded by the user.

The structural data used for segmentation and the diffusion weighted imaging data used for tractography based on spatial constraints from the segmentation are both in the subject space. Where the scans occur in a same examination with little or no movement of the patient within the MRI system, the segmentation locations are spatially aligned with the diffusion weighted data. Due to patient movement, different scan settings, or acquisition at different times, the structural data (e.g., T1 weighted image) may be misaligned relative to the diffusion weighted data. The structural data acquired in act 21 is acquired at a same time as the diffusion weighted data, so is less likely to be misaligned. Other structural data may better distinguish between tissues or objects for segmentation.

In act 30, the structural data for the patient is aligned with the data acquired without diffusion sensitization. For example, T1 data is registered with the field map corrected b0 data. The spatial transformation provided by the registration is used to find the locations in the structural data (e.g., T1) corresponding to locations in the diffusion weighted data and/or b0 or b0r data.

Any type of registration is performed to determine the alignment. Nonlinear registration is used, but linear registration may be used, such as where the patient motion may be minimal. The relative translation in three-dimensions, rotation in three-dimensions, and/or scale is calculated. Any elastic registration may be used. Intensity or feature-based registration may be used. In one embodiment, diffeomorphic non-rigid registration is performed. The T1 image is non-linearly registered to the field map-corrected b0 image.

After registration, a transformation is performed to relate locations between data sets, or the structural data is warped to the subject space defined by the field map-corrected b0 image. The segmentation of act 28 is performed using the warped data. For example, tissue segmentation for white matter, gray matter, and corticospinal fluid separation is applied to the warped T1 image to obtain white matter and gray matter masks, as well as a white matter-gray matter interface. Once warped, the segmentation of act 28 provides more spatially accurate masks relative to the diffusion weighed data.

Referring to FIG. 2, brain regions of interest, tracts, and tract path spatial restrictions are identified from atlases registered to a patient in act 14. The knowledge represented in a template or other form of atlas is converted to the subject space of the specific patient. The knowledge has spatial distribution, so that spatial distribution is registered to the subject space. Once registered, the spatial constraints or other information used for tractography may be incorporated from the generic template or other atlas. For example, the brain regions of interest define locations through which a given tract cannot or is likely to pass. As another example, the likely spatial locations of different common tracts are provided. In yet another example, the origin and/or end regions of particular tracts are provided.

More than one atlas may be used. For example, the automated anatomical labeling (AAL) atlas provides various brain regions of interest. Other atlases provide tract information, such as a JHU-DTI-Prob atlas providing 47 or other number of tracts with or without starting and ending regions. By registering both atlases to the subject space for a particular patient, generic or common brain regions and tracts may be used to seed (i.e., initiate) the tractography, act as spatial constraints on the tractography, and/or provide input for creating or following patient-specific tracts (e.g., information used in processing the diffusion weighted data into a tractogram).

FIG. 3 shows one example embodiment of act 14 incorporating knowledge from atlases. In act 35, fractional anisotropy (FA) data is determined. Diffusion tensors are fit to the denoised, corrected diffusion weighted data of the patient, providing a representative fractional anisotropy image in the subject space. Other fitting than tensors may be used. A function (e.g., tensor) representing the variation across the various volumes or frames of data of the diffusion weighted imaging data is fit to each voxel.

In this embodiment, the fractional anisotropy computation is performed since the atlas being used has the spatial distribution of information in its fractional anisotropy space. For example, the tracts of the JHU-DTI-Prob atlas are defined or spatially represented in or relative to a fractional anisotropy image. In other embodiments, the atlas provides the tract information relative to other types of data, such as structural data. In these other embodiments, act 35 converts to the appropriate type of data or is not provided as the appropriate type of data is already known (e.g., T1 volume).

The JHU-DTI-Prob atlas delineates the probabilistic maps of 47 important WM fiber tracts. For example, tracts for the corpus callosum, cortical spinal tract, and cingulum are provided. Probabilistic information may be included, such as representing a range of possibilities with corresponding likelihoods for each tract. These tract maps indicate group-averaged or template tract information used to perform a tract-specific spatially constrained tractography on the data for the specific patient. These tracts have spatial positioning relative to or are represented in the fractional anisotropy data of the atlas.

In act 36, the atlas is registered with the subject space. Any of the nonlinear types of registration discussed above may be used. Linear registration may be used. In the example of FIG. 3, the atlas and/or tracts are spatially represented by fractional anisotropy data, so this fractional anisotropy data is nonlinearly registered with the fractional anisotropy data created from the patient specific information in act 35.

In act 38, the tract maps are warped to the subject space based on the nonlinear registration. The nonlinear registration provides a transformation to convert between the coordinate systems. The tract maps from the atlas are warped using the transformation to provide the tract maps in the subject space. For example, the 47 group-averaged white matter tract maps in the JHU-DTI-Prob atlas are warped to the subject space represented by the fractional anisotropy data output from act 35. The resulting tract maps are an input to the diffusion tractography in act 16. The atlas information is integrated into the tractography.

The atlas as registered or warped may provide additional information than the tract maps. For example, tract-specific regions of interest are included in the JHU-DTI-Prob atlas with the track maps. The Template region of interest set (TRS) from the JHU-DTI-Prob atlas may be used to guide tractography (i.e., tract-specific spatial regions to be connected or avoided). The tract-specific regions as warped to the subject space are determined in act 46 to limit where tracts may occur (exclusion or inclusion spatial criteria) in the tractography of act 16. Act 46 may be optional or not performed or may be used instead of outputs of act 41. The tracts are spatially constrained as indicated by the regions from the JHU-DTI-Prob atlas.

Information from one or more other atlases may be integrated as well or instead. Different anatomical atlases may be used as templates for registration and brain parcellation.

In act 40, binary images of each of the labeled AAL regions are pruned to only include areas within the white matter-gray matter mask of the subject. This binary image is used as start and/or end regions or to spatially constrain fiber tracking. To use, the binary image is created in the subject space.

In act 42, the atlas with the relevant information is registered to the subject space. For example, the AAL and ICBM152 MNI atlases are in the same space by construction. The ICBM152 MNI atlas includes a structural template or set of data. By non-linearly registering the MNI atlas with the T1 or other structural data for the patient in act 42, the transformation to relate the coordinate systems of the AAL and the subject space are provided. In the example of FIG. 3, the structural representation of the MNI atlas is registered with the T1 structural data previously registered with the b0 data in act 30. Where b0 provides the subject space, the warped T1 also represents that subject space.

In act 44, the regions of interest of the AAL atlas are warped based on the nonlinear registration. Since the AAL atlas is in the MNI atlas space, the transform from act 42 is used to convert the AAL atlas region of interest information into spatial regions of interest in the subject space.

Returning to act 40, the warped AAL information is used to generate a binary AAL map in the subject space. The white matter-gray matter mask limits the regions of interest from AAL. A binary map of the start, end, or spatial constraint of fibers is output for tractography In act 41, regions of interest through which tracts pass are identified from another atlas. The AAL atlas provides regions of interest labels for the brain, but without the tract maps. The cerebral regions of interest are annotated in the AAL atlas and may include regions not included in other atlases. The AAL atlas is used to identify the cerebral regions of interest through which the tract maps in JHU-DTI-Prob atlas are passing. The JHU-DTI-Prob atlas provides the tracts, but with limited region information. For example, only the beginning, ending, or regions through which a tract cannot pass are provided. The AAL atlas may have more robust information or be better trusted than other atlases for region information.

In act 43, to provide the regions of interest relative to the tracts, the MNI atlas is registered with the JHU-DTI-Prob atlas. This registration relates the AAL atlas to the JHU-DTI-Prob atlas.

In act 45, for regions relative to the tracts, the AAL atlas is converted to the JHU atlas space. The result is the AAL atlas information spatially distributed in the JHU atlas space.

In act 41, the regions of interest through which the tracts pass are identified after the warping. The tracts in the JHU space are used to determine the regions of interest from AAL. The group-averaged white matter tracts in the JHU-DTI-Prob atlas are used to identify the AAL regions of interest each tract is passing through. This information is used to guide tractography. AAL output in act 40 provides AAL regions tuned or warped to the subject. The AAL ROI IDs output in act 41** provide region identifications used in tractography. These outputs may be used together so that warped tracts have include and/or exclude regions in the tractography.

In act 16 of FIGS. 2 and 3, a processor or MRI system generates a tractogram for a patient. The tractogram represents the white matter fiber tracts as occurring in the patient. The tractogram, personalized to the specific patient, is generated from the corrected diffusion weighted data output in act 34, the tract maps output from act 38, and the regions of interest output from act 41. Other information may be included, such as the template region of interest set output by act 46, the white matter mask output by act 28, and/or binary region masking output by act 40. Additional, different, or fewer inputs to the tractography operation may be used, such as not including the TRS of act 46, the white matter mask from act 28, and/or the binary images from act 40. In the embodiment of FIG. 3, processed DWI data, white matter mask, the white matter-gray matter interface image as a binary image, warped AAL ROIs, TRS, and tract maps are input for tractography for the computation and filtering of the tractogram(s).

The tractography solves for a function relating the diffusion of different directions for each voxel. While a diffusion tensor may be determined, other functions may be used. In one embodiment, fiber orientation distributions are solved for from the diffusion weighted imaging data. For modeling diffusion with fiber orientation distributions, a constrained spherical deconvolution is used. Other approaches for estimating diffusion may be used.

Based on seeding, masking, and other spatial constraints, the tractography uses the diffusion weighted imaging data and constrained spherical deconvolution-based diffusion estimation to find tracts for the patient corresponding to the atlas provided tracts. In addition to fitting the fiber orientation distributions to each voxel, the voxels belonging to different tracts are found. The deterministic tractography continues until the desired tracts are located. The probability information of the tracts may be used to test or sample for various tract paths as limited or guided by the brain regions of interest and masking using the seeding. The output of the tractography is a collection of tracts through the volume of the patient as a tractogram. The tractogram also indicates the diffusion anisotropy along any number of tracts through a brain of the patient.

The brain regions of interest, the tracts, and the tract path spatial restrictions are used to control the tracing of the tracts. For example, the tract-specific regions (TRS), the white matter mask, and the white matter-gray matter interface are used to restrict where the tracts may be located in the solution while the tracts are used to guide locating of the tracks in the diffusion weighted data. A region of interest-guided probabilistic tractography is performed. The regions are limited to white matter by the white matter mask. The regions of interest define starting points and/or restrictions on given tracts (e.g., inclusion or exclusion criteria). The tractography traces along each tract from voxel to voxel determining whether adjacent voxels are part of any given tract. The step size, maximum local curvature as a tract is traced, minimum fractional anisotropy to be considered part of a tract, and/or other tractography limitations are used to trace along each tract.

The track tracing is seeded by the white matter mask, the white matter-gray matter interface image (e.g., binary image), and the tracts. The seeding establishes where to initiate tractography.

The search may be limited. For example, the tractography or tract tracing is limited to white matter. Accordingly, the white matter mask masks the diffusion weighted data. Voxels of the data associated with white matter may be included in a tract, and voxels not of white matter are excluded.

The tracing may be spatially constrained in other ways. Inclusion and exclusion locations are provided by the brain regions of interest relative to each given tract and the tract path spatial restrictions (e.g., AAL, TRS).

In act 18 of FIG. 2, the tractogram is used for further analysis. The fiber orientation distribution and/or tracts are used to determine further information. For example, a statistical value is calculated from the fit function for each voxel. Any statistic may be used, such as a maximum or variance. As another example, data normalization standardizes the intensity from the tractogram or diffusion weighted data prior to tractography among data of multiple subjects. In another example, fiber clustering determines groups of fiber pathways or tracts for anatomically meaningful clusters. In yet another example, a biomarker or map computes one or more scalar maps (e.g., generalized) of fractional anisotropy, diffusivity, kurtosis, harmonics-driven features, etc.). In another example, different connectivity matrices are computed using the tractogram and anatomical ROIs for network construction. The origin and conclusion of the tracts as well as the tracts are formed into a network with region-specific nodes. Graphs may be constructed for network analysis. Additional modules or processes may be incorporated.

In act 20, an image is transmitted. The transmission is to a display, to a memory, or over a network to another device. For example, the image is displayed on a display of an MRI system. Alternatively, the image is displayed on a workstation, computer or other device. The image may be stored in and recalled from a PACS memory.

Figure 4:
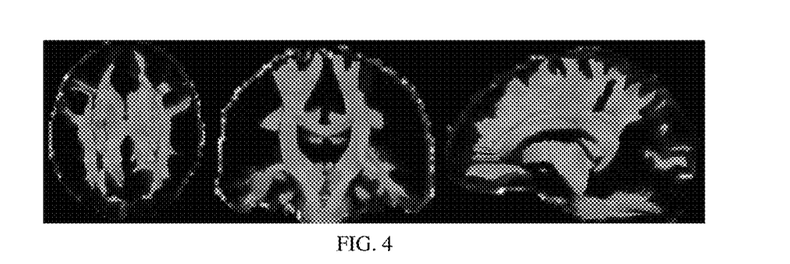
FIG. 4 shows example images from a multi-planar reconstruction of a tractogram.

The image is of the tractogram or information derived from the tractogram. A tractogram of white matter is output. FIG. 4 shows an example. The gray-scale of FIG. 4 is based on color coding with different colors coding diffusion intensity along three orthogonal directions (e.g., shades of red along one dimension, shades of blue along another dimension, and shades of yellow along another dimension). FIG. 4 shows three tractogram images corresponding the axial, coronal, and sagittal slices or planes through a volume represented by a set of data of the tractogram. 47 different tracts are included. Fewer tracks and/or different mapping of the fiber orientation distributions to display values may be used. The images represent white matter tracts in the brain based on the anisotropy of water diffusion within the brain.

Other images may be generated with the tractogram. For example, an image representing brain structure is generated from T1 data. The tractogram is overlaid on the structure image or displayed adjacent to the structure image.

The image is a two-dimensional image or a three-dimensional rendering to a two-dimensional display from voxel data representing three-dimensions. The image is generated from a distribution of tracts and/or anisotropy of diffusion in three dimensions.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed is:

1. A method for tractography with magnetic resonance imaging, the method comprising:
    scanning a patient with a magnetic resonance imaging system for diffusion weighted data, the scanning providing data without diffusion sensitization and in phase-encoded and reverse phase encoded directions, the diffusion weighted data being in a subject space;
    acquiring, with the magnetic resonance imaging system, structural magnetic resonance data;
    correcting the diffusion weighted data with field maps estimated from the data acquired in the phase encoding and reverse phase encoding directions;
    denoising the corrected diffusion weighted data;
    registering a first atlas of tract maps to the subject space;
    identifying regions of interest through which tracts of the tract maps pass from a second atlas;
    generating a tractogram for the patient from the denoised, corrected diffusion weighted data, the tract maps, and the regions of interest; and
    transmitting an image of the tractogram.

2. The method of claim 1 wherein scanning comprises performing diffusion magnetic resonance imaging.

3. The method of claim 1 wherein correcting comprises field map correcting.

4. The method of claim 1 wherein denoising comprises performing local principle component analysis.

5. The method of claim 1 wherein registering comprises registering the tract maps as probabilistic maps of fiber tracts.

6. The method of claim 1 wherein registering comprises determining first fractional anisotropy data from a fit of diffusion tensors to the denoised, corrected diffusion weighted data of the patient, nonlinearly registering the first fractional anisotropy data to second fractional anisotropy data of the first atlas, and warping the tract maps to the subject space based on the nonlinear registration.

7. The method of claim 1 wherein identifying comprises nonlinearly registering structural data representing the patient to structural data linked to the second atlas, warping the regions of interest of the second atlas based on the nonlinear registering, and identifying the regions of interest through which the tracts pass after the warping.

8. The method of claim 1 wherein generating comprises modeling diffusion with fiber orientation distributions from a constrained spherical deconvolution.

9. The method of claim 1 wherein generating comprises performing deterministic tractography guided by the regions of interest as seeded by the tract maps.

10. The method of claim 1 wherein transmitting comprises transmitting the image color coded as an axial tractogram, coronal tractogram, sagittal tractogram, or combinations thereof.

11. The method of claim 1 further comprising determining tract-specific regions as spatial constraints for the tracts from the first atlas, wherein generating the tractogram comprises generating the tractogram from the tract-specific regions.

12. The method of claim 1 further comprising:
    masking skull from the diffusion weighted data;
    registering the structural data for the patient with the data in the phase encoded direction; and
    segmenting white matter and a white matter-gray matter interface from the structural data as registered;

wherein generating the tractogram comprises generating the tractogram from the white matter and the white matter-gray matter interface.

13. The method of claim 1 further comprising:

clustering tracts of the tractogram;

computing a biomarker map from the tractogram;

constructing a network or graph of the tracts of the tractogram; or combinations thereof.

\* \* \* \* \*